United States Patent [19]

Zawadiak et al.

[11] Patent Number: 5,990,357

[45] Date of Patent: *Nov. 23, 1999

[54] PROCESS FOR THE OXIDATION OF ISOALKYLAROMATIC HYDROCARBONS, AND CATALYST FOR THE EXECUTION OF THE PROCESS

[75] Inventors: Jan Zawadiak; Zbigniew Stec, both of Gliwice, Poland; Ulrich Knips, Kamen; Robert Zellerhoff, Hamminkeln, both of Germany; Danuta Gilner, Gliwice, Poland; Beata Orlinska, Katowice, Poland; Jerzy Polaczek, Warszawa, Poland

[73] Assignee: Rutgers Kureha Solvents GmbH, Duisburg, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/821,019

[22] Filed: Mar. 19, 1997

[30] Foreign Application Priority Data

Mar. 20, 1996 [PL] Poland ..................................... 313418

[51] Int. Cl.⁶ .......................... C07C 45/00; C07C 409/00
[52] U.S. Cl. ........................ 568/320; 568/557; 568/910.5
[58] Field of Search ..................................... 568/320, 557, 568/910.5; 502/164, 169

[56] References Cited

U.S. PATENT DOCUMENTS

| 3,898,288 | 8/1975 | De-Radzitzky D'Ostrowick . |
| 4,362,821 | 12/1982 | Lin . |
| 4,448,892 | 5/1984 | Kukes ...................................... 502/164 |
| 4,879,266 | 11/1989 | Bhattacharya . |

FOREIGN PATENT DOCUMENTS

| 0267759 | 5/1988 | European Pat. Off. ........ C07C 29/50 |
| 0309005 | 4/1929 | United Kingdom . |
| 9520560 | 8/1995 | WIPO . |

OTHER PUBLICATIONS

Hawley's Chemical Dictionary 12th edition p. 931, 1993.
Defensive Publication of the Patent office by Aufdermarsh T856,021 (Nov. 12, 1968).
CA 123: 256345 abst of JP 07196573, Aug. 1, 1995.
React. Kinet. Catal. Lett.; vol. 27 (2) No. 2, 231–233 (1985), Entitled: "The Use of Phase—Transfer Catalysis For the Initiation of p–Xylene Oxidation".

*Primary Examiner*—Paul J. Killos
*Assistant Examiner*—Jean F Vollano
*Attorney, Agent, or Firm*—Hedman, Gibson & Costigan, P.C.

[57] ABSTRACT

In a process for the catalytic oxidation of isoalkylaromatic hydrocarbons into ketones, alcohols and peroxides the isoalkyl-aromatic hydrocarbons in fluid phase at a temperature of 60 to 120° C. are oxidized by oxygen in the presence of a catalyst of metal salt of different valency and alkylammonium salt or alkylphosphonium salt. Further there is claimed a catalyst for the oxidation of isoalkylaromatic hydrocarbons, containing a metal salt selected from copper salts, cobalt salts and manganese salts or their mixtures and an alkylammonium salt or alkylphosphonium salt in a ratio of metal salt to alkylammonium salt or alkylphosphonium salt of 0.5 to 50:1.

4 Claims, No Drawings

PROCESS FOR THE OXIDATION OF ISOALKYLAROMATIC HYDROCARBONS, AND CATALYST FOR THE EXECUTION OF THE PROCESS

The invention relates to the catalytic oxidation of isoalkylaromatic hydrocarbons as well as to a catalyst for the execution of this reaction.

The oxidation of isoalkylaromatic hydrocarbons into organic ketones, alcohols and peroxides is of great industrial importance and is used mainly for the production of isoalkylaromatic hydroperoxides, the decomposition of which leads to the formation of corresponding hydroxyaromatic compounds. It has also been endeavored to recover organic peroxides from these raw materials.

From PL 156 813 there is known a process for the recovery of dicumyl peroxide by reaction of cumene with cumyl hydroxyperoxide. JP 6 049 191 describes the recovery of dicumyl peroxide by condensation of cumyl hydroperoxide with 2-phenyl-2-propanol. From CZ 198 876 it is a known practice to recover dicumyl peroxide by direct oxidation of the cumene with air in the presence of iron capronate at a temperature of 94° C. This reaction, however, proceeds very slowly. The product obtained after 65 hours contained 21.7% of dicumyl peroxide, 12.5% of acetophenone and 22.2% of 2-phenyl-2-propanol.

In Neftekhimiya, vol. 11, 1971, 862–866 there was also discussed the recovery of bis-2-isopropylnaphthyl peroxide, 2-isopropylnaphthyl alcohol by means of oxygen in the presence of copper(II)-nitrate and azodiisobutyronitrile, at a temperature of 95° C. After 68 hours, the product obtained contained 34.1 mol % of bis-2-isopropylnaphthyl peroxide, 9.4 mol % of 2-isopropylnaphthyl alcohol and 1.2 mol % of 2-acetyl naphthalene.

These known processes are characterized by a long reaction time of more than 10 hours, and an inadequate conversion of the hydrocarbon used, which ordinarily does not exceed 60%. The practical and in particular the industrial utility of these processes is, therefore, limited.

The problem underlying the invention, therefore, is to provide a process that delivers greater yields in organic ketones, alcohols and peroxides in the oxidation of isoalkylaromatic hydrocarbons.

This problem is solved by the catalytic oxidation of isoalkylaromatic hydrocarbons in the fluid phase, in which a metal salt of different valency and an alkylammonium salt or alkylphosphonium salt are used as catalyst and the reaction is carried out at a temperature of 60 to 120° C.

The invention relates, further, to a catalyst for the execution of this oxidation, which contains a metal salt and an alkylammonium salt or an alkylphosphonium salt. According to the invention preferred metal salts of different valency are copper salts, cobalt salts and manganese salts or mixtures of these salts. Anions of these metal salts suitable according to the invention are chlorides, bromides, iodides, nitrates, sulfates, hydrogen sulfates or sulfonates. Further, the anion can be a fatty acid anion such as stearate, palmitate and myristate.

Alkylammonium salts and alkylphosphonium salts preferred according to the invention are those which preferably have an alkyl radical with 3 to 20 carbon atoms, and wherein the anion can be a chloride, bromide, iodide, nitrate, sulfate, hydrogen sulfate or sulfonate.

The molar ratio of the metal salt of different valency to the alkylammonium salt or alkylphosphonium salt is 0.5 to 50:1.

Reactants to be used according to the invention are isoalkyl-aromatic substances of the general formula Ar-CHRR', in which R and R' are the same or different and represent methyl, ethyl or propyl. Ar represents phenyl and its homologues as well as naphthyl and its homologues. Homologues of phenyl are, for example, toluyl, benzyl or xylyl as well as phenyl substituted by one or methyl and/or ethyl groups, homologues of naphthyl are their methyl derivatives and ethyl derivatives.

Preferred reactants of the process according to the invention are isopropyl- or aromatic isobutylaromatic substances such as cumene, p-tert.-butylcumene (TBK), isopropyl naphthalene (IPN), isobutyl naphthalene and 2,6-diisopropyl naphthalene. A precondition for carrying out the process of the invention is the presence of a tertiary hydrogen atom in alpha-position on the aromatic ring. If 2-isopropyl naphthalene is used as reactant, the simultaneous presence of 1-isopropyl naphthalene is uncritical.

The reactants are converted at 60 to 120° C. in the presence of the catalyst, it being possible to add the catalyst to the fluid reactants. At the reaction temperature the reactants are present in fluid form. The molar ratio of reactant to metal salt amounts in the process of the invention is preferably 4000:1 to 80:1. The molar ratio of metal salt of different valency to aklylammonium salt or alkyl phosphonium salt is preferably 0.5 to 50:1. The process is performed without pressure. The reaction time is 2 to 20 hours.

Process products of the process of the invention are arylalkyl ketones of the general formula Ar—CO—R, arylalkyl carbinols of the general formula Ar—CRR'OH and di-(arylalkyl peroxides) of the general formula Ar—CRR'—O—O—CRR'—Ar, in which Ar, R and R' have the signification given above. Examples of the ketones obtained according to the invention are acetonaphthone, acetophenone and 2,6-diacetylnaphthalene. Examples of arylalkyl carbinols obtained according to the invention are 2-(2-naphthyl)isopropanol and cumyl alcohol.

Examples of the diarylalkyl peroxides obtained according to the invention are tertiary symmetrical bis[1-alkyl-1-1(1-or 2-naphthyl) alkyl] peroxides.

In dependence on the chosen oxidation conditions with the process of the invention in a short time there can be achieved a concentration of organic peroxides of about 20% by weight, or alcohol and ketone concentrations of more than 45% by weight in the product mixture. These products are valuable intermediate products for organic syntheses by means of esterifications, dehydrogenations and oxidations. Organic peroxides are usable as initiators and cross-linking catalysts in the production of rubber.

The following examples serve for the explanation of the invention.

EXAMPLE 1

In a glass reactor with a volume of 40 $cm^3$, which is equipped with an agitating mechanism, a reflux cooler, a bubbling throttle, a thermometer and a heating mantle, there are introduced 0.28 mole of cumene, $2.56 \times 10^4$ mole of copper(II)-chloride dihydrate, and $5.36 \times 10^4$ mole of tetrabutylammonium bromide (TBAB) and the reaction mixture is then warmed to 110° C. under action of molecular oxygen, which is led through at a rate of 15 $dm^3/h$ for twelve hours. The end product contains 32.5% by weight of dicumyl peroxide, 18.6% by weight of 2-phenyl-2-propanol and 23.6% by weight of acetophenone.

Examples 2 to 11 are carried out in the same manner. The reaction conditions and results are given in the following table.

We claim:

TABLE

| Example | Raw material | Temperature (°C.) | Oxygen passage (dm³/h) | Time (h) | Catalytic system Metal salts (mol*10³) | Onium salts (mol*10⁵) | Composition of the product Peroxide (% by wt) | Ketone (% by wt) | Carbinol (% by wt) |
|---|---|---|---|---|---|---|---|---|---|
| 2 | Cumol | 110 | 15 | 8.5 | 2.56 CuCl$_2$.2H$_2$O | 5.32 TBAB | 15.0 | 41.0 | 37.0 |
| 3 | Cumol | 110 | 2 | 4.0 | 0.26 CuCl$_2$.2H$_2$O | 53.20 TBAB | 22.6 | 18.2 | 21.6 |
| 4 | Cumol | 70 | 15 | 4.0 | 12.80 CuCl$_2$.2H$_2$O | 53.20 TBAB | 10.7 | 16.4 | 39.0 |
| 5 | Cumol | 110 | 15 | 2.0 | 2.56 CoCl$_2$.6H$_2$O | 5.32 TBAB | 11.7 | 23.4 | 39.0 |
| 6 | Cumol | 110 | 15 | 5.0 | 2.56 copper(II) stearate | 5.32 TBAB | 11.0 | 28.6 | 38.4 |
| 7 | Cumol | 110 | 15 | 5.0 | 2.56 CuCl$_2$.2H$_2$O | 5.32 TBAHSO$_4$* | 17.4 | 35.0 | 37.0 |
| 8 | Cumol | 110 | 15 | 6.0 | 2.56 CuCl$_2$.2H$_2$O | 5.32 TBPhCl** | 19.0 | 29.0 | 35.0 |
| 9 | 2-IPN | 110 | 15 | 1.5 | 2.56 CuCl$_2$.2H$_2$O | 5.32 TBAB | 16.8 | 31.5 | 31.2 |
| 10 | TBK | 110 | 15 | 2.5 | 2.56 CuCl$_2$.2H$_2$O | 5.32 TBAB | 17.4 | 28.7 | 32.4 |
| 11 | 2,6-DIPN | 110 | 15 | 4.0 | 2.56 CuCl$_2$.2H$_2$O | 5.32 TBAB | 20.5 total peroxide | not determined | not determined |

*TBAHSO$_4$ — Tetrabutylammonium hydrosulfate
**TBPhCl — Tetrabutylphosphonium chloride 1. Process for the catalytic oxidation of isoalkylaromatic hydrocarbons into ketones, alcohols and peroxides, comprising the oxidation of the isoalkylaromatic hydrocarbons in the fluid phase at a temperature of 60 to 120° C. by oxygen in the presence of a catalyst composed of one or several metal salts selected from the group consisting of copper salts, manganese salts and cobalt salts, and of an alkylammonium salt or an alkylammonium salt, whereby said process produces from 10.7% to 22.6% by weight of peroxide as a product.

2. Process for the catalytic oxidation of isoalkylaromatic hydrocarbons into ketones, alcohols and peroxides, comprising the oxidation of the isoalkylarmoatic hydrocarbons in the fluid phase at a temperature of 60 to 120° C. by oxygen in the presence of a catalyst composed of a copper salt, and of an alkylammonium salt or an alkylphosphonium salt.

3. Process according to claim 1 wherein the alkylammonium salt has at least one alkyl residue with 3 to 20 carbon atoms.

4. Process according to claim 2 wherein the alkylammonium salt has at least one alkyl residue with 3 to 20 carbon atoms.

* * * * *